United States Patent [19]

Vilardi

[11] 4,226,669

[45] Oct. 7, 1980

[54] VACUUM CENTRIFUGE WITH MAGNETIC DRIVE

[75] Inventor: Frank Vilardi, Nesconset, N.Y.

[73] Assignee: Savant Instruments, Inc., Hicksville, N.Y.

[21] Appl. No.: 37,429

[22] Filed: May 9, 1979

[51] Int. Cl.$^3$ .............................................. B01D 1/00
[52] U.S. Cl. ............................... 159/6 R; 192/84 PM; 233/26; 200/61.7; 159/44
[58] Field of Search ................ 159/6, 44; 192/84 PM; 233/23, 26; 200/61.7

[56] References Cited

U.S. PATENT DOCUMENTS

| | | | |
|---|---|---|---|
| 2,512,604 | 6/1950 | Bierwirth | 159/6 R |
| 3,304,990 | 2/1967 | Ontko et al. | 192/84 PM |
| 3,504,777 | 4/1970 | Waugh | 200/61.7 |
| 3,512,618 | 5/1970 | Schafer | 192/84 PM |

*Primary Examiner*—Norman Yudkoff
*Attorney, Agent, or Firm*—Edward F. Levy

[57] ABSTRACT

A high speed centrifugal concentrator includes a vacuum chamber within which a centrifuge rotor is rotatably mounted for spinning a plurality of vials containing biological solutions or the like at high speed while subjecting the solution to a vacuum condition for concentrating and evaporating the latter. The vacuum chamber has a hinged cover and is completely enclosed to maintain the vacuum condition therein and the centrifuge rotor is driven by an electric motor located outside of said closed vacuum chamber and remote therefrom. The electrical circuit for driving the motor includes dynamic braking means for braking the motor in response to manual operation of a selector switch, or to the raising of the vacuum chamber cover from closed position.

10 Claims, 6 Drawing Figures

VACUUM CENTRIFUGE WITH MAGNETIC DRIVE

The present invention relates to apparatus for the separation and concentration of biological material, and in particular to a high-speed centrifugal concentrator which operates under vacuum to prepare dried samples of laboratory specimens.

In laboratory analysis projects, it is often necessary to prepare absolutely dried samples of a liquid specimen in preparation for use in amino acid analyzers, gas chromatography, mass spectrometers and other microchemical procedures where maximum sample concentration is essential. In order to dry such samples, a vacuum is customarily applied thereto in a vapor chamber. However, the applied vacuum causes "bumping" or foaming in certain solvents such as organic acids, mineral acids, and aqueous or volatile organic solvents, causing splashing, smearing and other defects in the dried sample.

Attempts have been made to eliminate the aforementioned foaming tendency by centrifuging the samples while the vacuum is applied thereto. This technique is effective in preventing undesirable foaming since as bubbles form in the material, they burst immediately. Up to the present time, however, the apparatus devised for such vacuum centrifuging operation has been found to be ineffective or to present difficulties. In some instances, the electric motor for driving the centrifuge was located outside of the vacuum chamber so that the motor drive shaft extended through the wall of the vacuum chamber and was connected to the centrifuge rotor within the chamber. Since this type of structural arrangement requires that the motor shaft extend through the wall of the vacuum chamber, expensive sealing means is required therefor, but such sealing means is subject to wear during use and has proved to be ineffective in maintaining the vacuum within the chamber without leakage.

In another attempt to provide an operative vacuum centrifuge device, the drive motor has been mounted within the vacuum chamber itself. This has been found disadvantageous for a variety of reasons. The heat generated by the operating motor interferes with the vacuum produced; the mounted motor is inconveniently inaccessible for servicing; and there is still the necessity for passing lead wires from the motor to the exterior of the vacuum chamber and providing adequate seals for such wiring.

It is an object of the present invention to provide a high speed centrifugal concentrator in which biological solutions or other fluid specimens contained in vials or test tubes are subjected to centrifugal action within a vacuum chamber thereby achieving rapid evaporation and solidification of the solution, with the combined vacuum and centrifugal action eliminating foaming in the solution as it evaporates.

Another object of the invention is the provision of a high speed concentrator of the type described in which fluid specimens are subjected to effective vacuum conditions within a closed and sealed vacuum chamber while being rotated and subjected to centrifugal action by a motor located exteriorly of and remote from the vacuum chamber.

Another object of the invention to provide a high speed centrifugal concentrator which includes a completely enclosed vacuum chamber in which a centrifuge rotor is mounted for rapid rotation and an electric motor is mounted exteriorly of the vacuum chamber and is magnetically coupled to the centrifuge rotor for driving the latter.

Still another object of the invention is the provision of a high speed centrifugal concentrator of the character described in which the vacuum chamber has a hinged cover which provides an air-tight seal for the vacuum chamber when in closed position and which has associated safety interlock means for deenergizing the motor when the cover is raised from its closed position.

A further object of the invention is the provision of a high speed centrifugal concentrator of the character described which includes means for dynamically braking the motor which is selectively operable when it is desired to halt action of the centrifuge, and is automatically operable when the cover is raised.

In accordance with the invention there is provided a high speed centrifugal concentrator comprising a housing which is divided into a vacuum chamber and a base section. The vacuum chamber has side and bottom walls and a hinged cover constituting the top wall thereof and being movable to a closed position in which it closes off said vacuum chamber in sealed, air-tight condition. The concentrator also includes a centrifuge rotor, means mounting the centrifuge rotor for rotation within the vacuum chamber, a drive motor for said centrifuge rotor mounted within said base section externally of said vacuum chamber and remote therefrom, and magnetic coupling means for providing a magnetic drive connection between said motor and said centrifuge rotor and creating a magnetic field passing through a wall of said vacuum chamber, whereby said centrifuge rotor is rotated within said vacuum chamber in response to operation of said drive motor.

The centrifuge rotor is removably mounted on a mounting shaft journalled in said vacuum chamber, and said magnetic coupling means comprises a first permanent magnet member secured to said mounting shaft and a second permanent magnet member secured to the drive shaft of the motor, with said permanent magnet members being closely spaced from each other on opposite sides of a wall of the vacuum chamber and arranged to create a magnetic field through said wall whereby said magnetic members are magnetically attracted to each other.

The concentrator also includes electrically-operable means for dynamically braking the motor which is selectively operable when it is desired to halt rotation of the centrifuge rotor, and is automatically operable when the hinged cover is lifted from its closed position.

Additional objects and advantages of the invention will become apparent during the course of the following specification when taken in connection with the accompanying drawings, in which.

Figure 1:
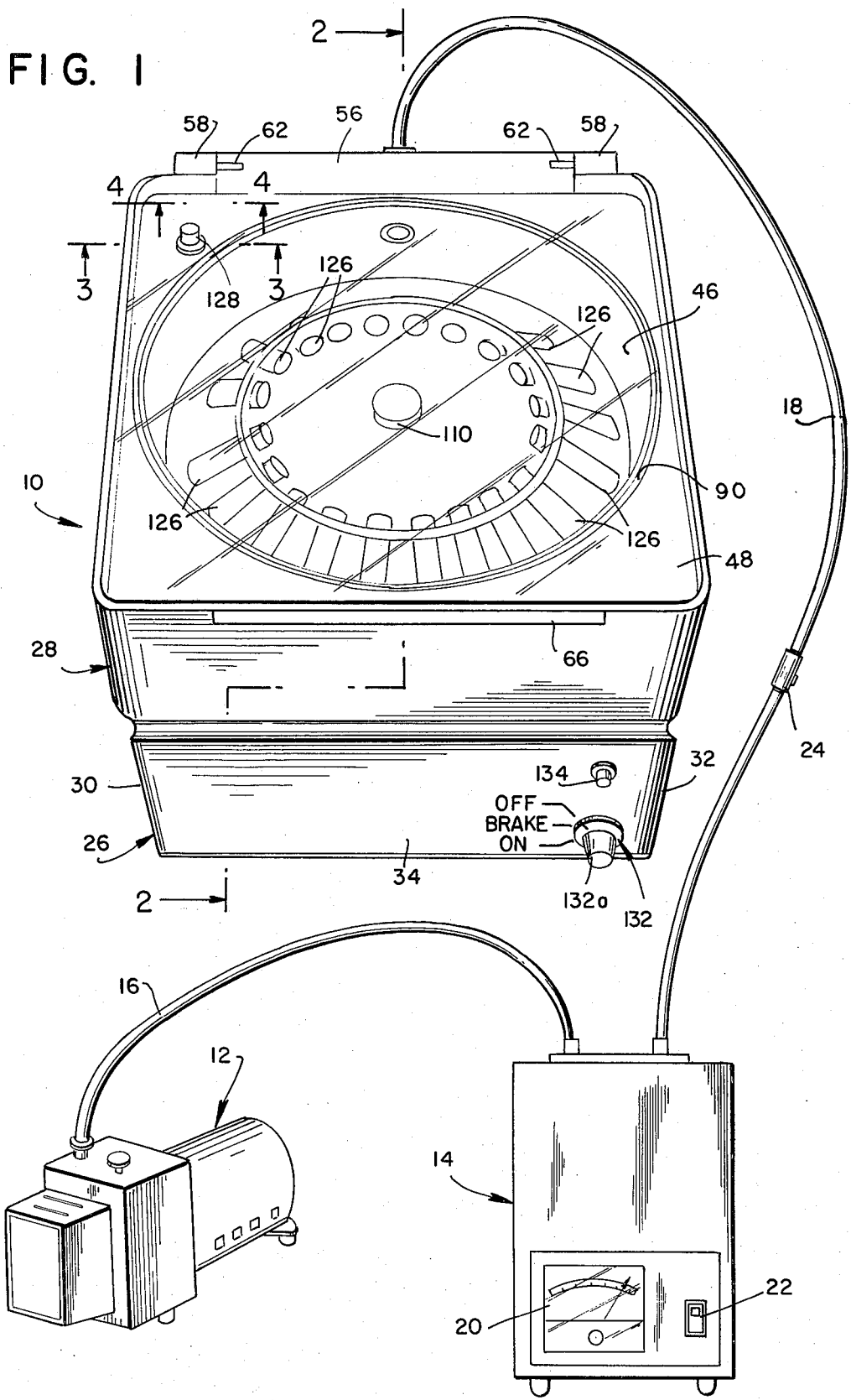
FIG. 1 is a perspective view of a high speed centrifugal concentrator and associated vacuum pump means, made in accordance with the present invention.

Referring in detail to the drawings, there is shown in FIG. 1, a vacuum concentrator and evaporator assembly made in accordance with the present invention. The assembly includes a vacuum centrifuge 10, a vacuum pump 12 and a refrigerated condensation trap 14. The vacuum pump is connected by a tube 16 to the trap 14, and the latter is in turn connected to the vacuum chamber of the centrifuge 10 by a tube 18. When the pump 12 is operated, it creates a vacuum in the centrifuge 10 through the trap 14. The vapor of the evaporated liquid in the centrifuge is condensed and retained in the refrigerated trap 14, and a meter 20 on the trap housing indicates the degree of vacuum in the centrifuge 10. The refrigerated trap 14 also has an on-off switch 22 by means of which the vacuum source may be shut off when desired, and a bleeder valve 24 in the tube 18 is selectively operable to enable air to be bled back into the vacuum chamber of the centrifuge 10.

The vacuum centrifuge concentrator 10 comprises a base housing 26 and a vacuum chamber 28 mounted thereon. The base housing 26 is preferably made of steel and is hollow and of square shape, having side walls 30, 32, front and rear walls 34 and 36, a removable bottom wall 38 and an open top which is covered over by the vacuum chamber 28. The removable bottom wall is attached to the vacuum chamber by means of screws 40 which are threaded into brackets 42 secured to the front, rear and side walls of the chamber. Secured to the under surface of the bottom wall 38 are rubber legs 44 which support the base housing 26 upon a table surface.

The vacuum chamber 28 has a housing made of aluminum and having a square cross-section the same as or slight larger than the cross-section of base 26. As shown in FIG. 1, the chamber housing is formed with a large central cylindrical cavity 46 which opens through the top wall 48 thereof, and within which the centrifuge rotor is mounted, in a manner to be presently described. The housing has a bottom wall 50, shown in FIG. 2, which overlies four elongated, L-shaped mounting brackets 52 secured along the top ends of the base front wall 34, rear wall 36 and side walls 30, 32, and the bottom wall 50 is connected to the top flanges of brackets 52 by screws 53, whereby the vacuum chamber 28 is securely mounted upon the base housing 26.

Figure 4:
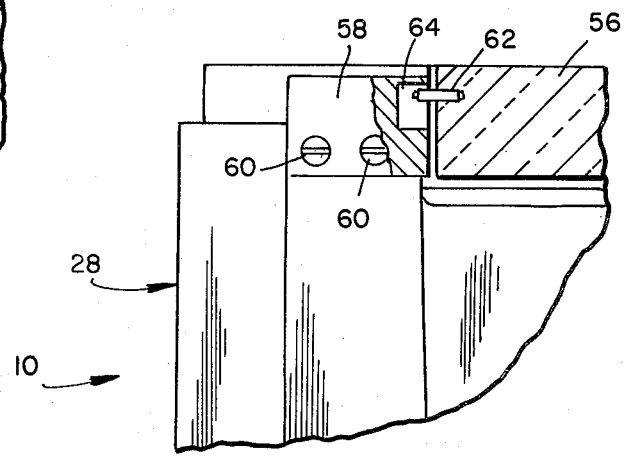
FIG. 4 is an enlarged elevational view of the cover hinge structure as viewed along line 4—4 of FIG. 1, with portions thereof shown in section to reveal inner construction.

The top wall 48 of the vacuum chamber 28, and the upper end of the central cavity 46 are covered over by a hinged cover 54 which is preferably transparent and may be made of a plate of rigid plexiglass approximately one-half inch thick. The cover 54 has an integral rearwardly-projecting extension portion 56 which fits between a pair of hinge blocks 58 which are attached to the rear wall portion of the vacuum chamber housing 28 by screws 60, as shown in FIG. 4. Pivot pins 62 are embedded in each side of the cover extension portion 56 and project therefrom into elongated slots 64 in the respective hinge blocks 58, so that the cover 54 may turn on said pivot pins between a lowered closed position and an elevated open position. At its front end, the cover 54 is provided with an integral forwardly-projecting handle portion 66 which may be conveniently grasped by the user for lifting the cover.

Figure 2:
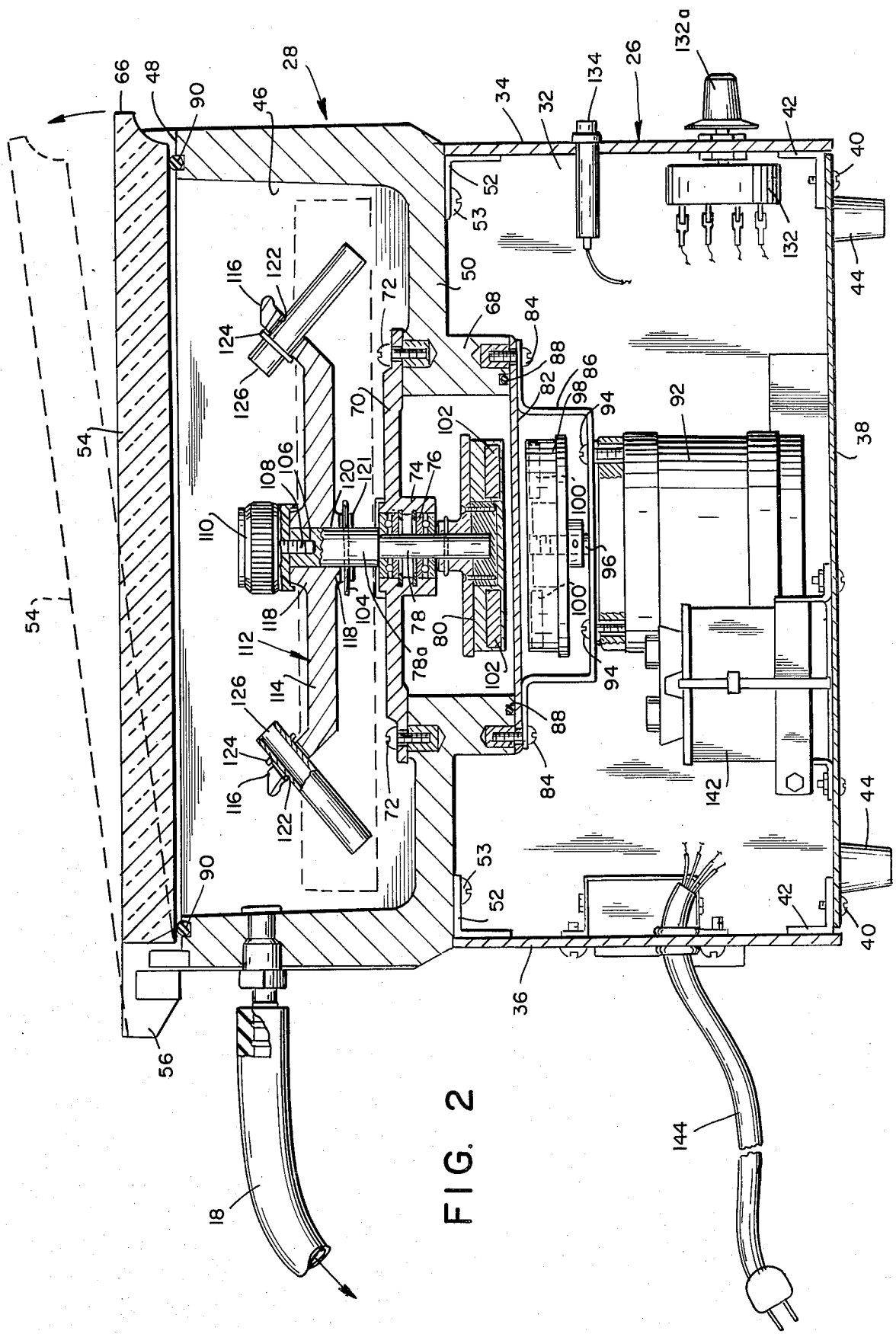
FIG. 2 is a sectional view of the centrifugal concentrator taken along line 2—2 of FIG. 1.
Figure 5:
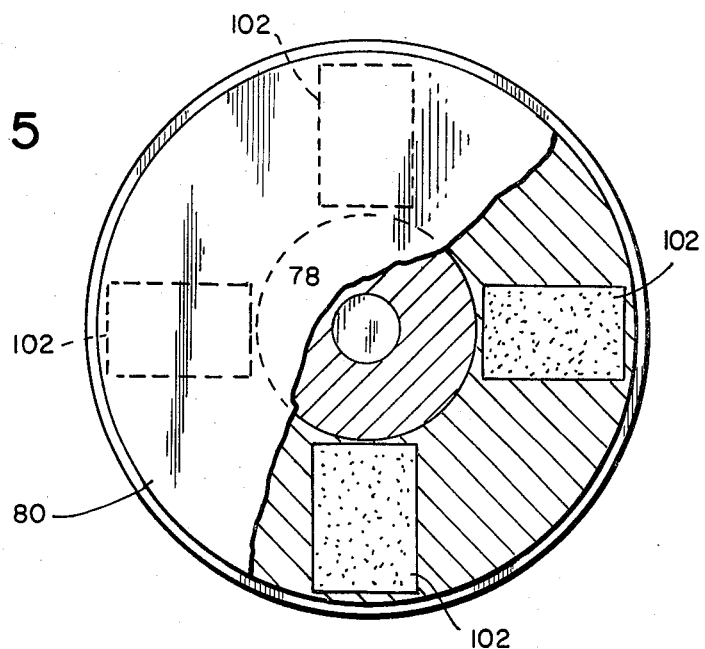
FIG. 5 is a plan view of one of the magnetic coupling discs employed to provide a drive connection between the motor and the centrifuge rotor.

A cylindrical enclosure or well 68 is formed centrally in the bottom wall 50 of the vacuum chamber housing, concentrically with the cylindrical cavity 46. The cylindrical well 68 depends from the bottom wall 50 and projects into the interior of the hollow base housing 26, as shown in FIG. 2. The top end of the well 68 is closed off by a cover plate 70 affixed to the bottom wall 50 by screws 72. The cover plate 70 is formed with a central bushing 74 containing a ball bearing assembly 76. Extending through, and journalled within the ball bearing assembly 76 is a mounting shaft 78 for the centrifuge rotor, the shaft 78 having a circular magnetic coupling disk 80 secured to the bottom end thereof.

The bottom end of the cylindrical well 68 is covered over by a closure plate 82 connected to the bottom wall surface of well 68 by screws 84 which also secure a motor mounting bracket 86 to the well 68. An elastomeric O-ring 88 is embedded in the bottom surface of the wall of well 68, and the screws 84 press the closure plate 82 firmly against said O-ring 88 to provide an air-tight seal at the bottom of the vacuum chamber 28. A similar elastomeric O-ring 90 is also embedded in the top surface of the vacuum chamber top wall 48, said O-ring being engaged by the cover 54 in its closed position to provide an air-tight seal at the top of the vacuum chamber 28. The cavity 46 of the vacuum chamber is thus completely enclosed and air-tight, to retain the vacuum formed therein.

A high-speed electric motor 92 is rigidly secured to the motor mounting bracket 86 by screws 94. The motor 92 has a drive shaft 96 which extends upwardly through an aperture in the mounting bracket 86, and upon the end of which is securely mounted a circular magnetic coupling disc 98.

Embedded in the coupling disc 98 are four equally-spaced permanent magnets 100. In a similar manner, four equally-spaced permanent magnets 102 are embedded in the magnetic coupling disc 80. As shown in FIG. 2, the magnets 100 are set within the coupling disc 98 with one pole thereof, for example the negative pole, located at the upper face of disc 98, while the magnets 102 are set within the coupling disc 80 with the opposite, positive poles thereof located at the lower face of disc 80. The coupling discs 80 and 98 are mounted with their magnetic faces closely spaced from the closure plate 82, on opposite sides thereof, so that they exert strong magnetic attraction to each other. Thus, when the coupling disc 98 is rotated by motor 92, the four magnets 100 remain in registry with the four magnets 102 of the closely-spaced disc 80, and the coupling disc 80 and its connected rotor mounting shaft 78 are rotated correspondingly by the strong magnetic field.

The rotor mounting shaft 78 has an upper portion 78a of enlarged diameter having a retaining pin 104 extending diametrically therethrough and projecting at both ends therefrom. At its top end, the shaft extension 78a is formed with an axial threaded bore 106 which is sized to receive a screw shank 108 projecting from the center of a retainer knob 110.

The mounting shaft 78 is adapted to rotate a centrifuge rotor 112, one or more of which may be provided with the centrifuge assembly 10. The rotor 112 is made of aluminum or rigid plastic and is in the form of a circular plate 114 having an upturned marginal flange 116 and a thickened hub portion 118. The hub portion 118 is formed with a central through bore 120 which is sized to receive the enlarged upper portion 78a of mounting shaft 78. In mounting the rotor 112 on the shaft 78, the retainer knob 110 is unscrewed and removed, the rotor 112 is placed on the shaft upper portion 78a with the latter received in the bore 120, and a groove 121 in the lower surface of the rotor hub 118 receiving the retaining pin 104. The screw shank 108 of the retainer knob 110 is then inserted in the threaded bore 106 of shaft portion 78a and turned therein. As the knob 110 is tightened, it clamps the rotor hub 118 rigidly against the pin 104.

The centrifuge rotor 112 is provided with one or more annular rows of apertures 122 into which are inserted hollow plastic tube holders 124. Each of the tube holders 124 is sized to receive a test tube 126 containing a supply of fluid to be subjected to the action of the centrifuge. In the embodiment illustrated in FIG. 1, the rotor 112 is shown as having twenty apertures 122 for mounting twenty test tubes 126. Alternative rotors may be provided for mounting a different number of tubes or for mounting tubes of different sizes. The centrifuge assembly may be supplied with a variety of different rotors having, for example, forty tube apertures, one hundred tube apertures, twenty-four tube apertures, or twelve apertures and eight apertures for mounting test tubes of larger diameter.

Figure 3:
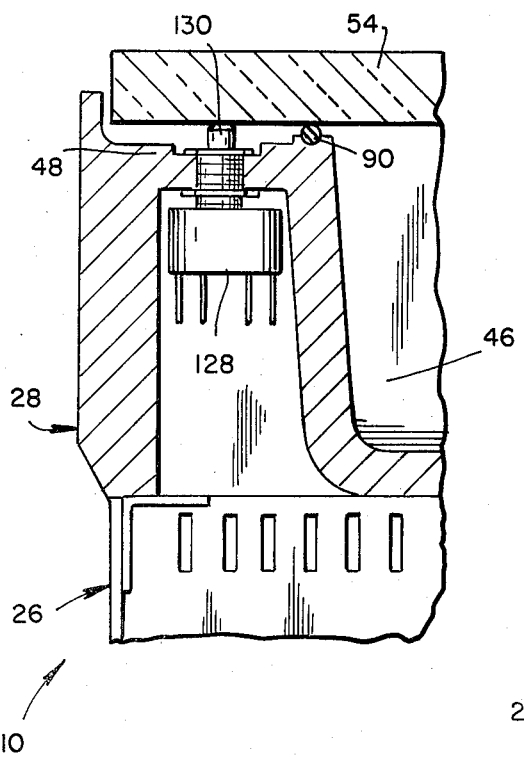
FIG. 3 is an enlarged sectional view taken along line 3—3 of FIG. 1.

As shown in FIGS. 1 and 3, the vacuum centrifuge 10 is provided with a safety interlock switch 128 which permits the electric motor 92 to be energized ony when the cover 54 is in closed position, and deenergizes the motor 92 when the cover 54 is lifted. The safety switch 128 is mounted on the top wall 48 of the vacuum chamber 28, and is of the push-button type, having a spring-biased plunger 130 projecting above said top wall 48, in a position to be engaged and depressed by the hinged cover 54 when the latter is brought to closed position. The depressed plunger 130 closes the contacts of switch 128, thereby completing the circuit to the motor 92.

The energizing circuit for the motor 92 includes means for dynamic braking of the motor 92, which means are operated alternatively by the interlock switch 128 or by a rotary selector switch 132 mounted on the front wall 34 of the base housing 26. As shown in FIG. 1, the rotary selector switch 132 has a knob 132a which is movable between a first "Off" position in which the switch deenergizes the electric motor 92, a second "On" position in which electrical power is supplied to the motor, and a "Brake" position in which dynamic braking is applied to the rotating motor. Also mounted on the front wall 34, immediately above the selector switch 132 is an indicator light 134 which is illuminated when the selector switch 132 is in the "On" position.

Figure 6:
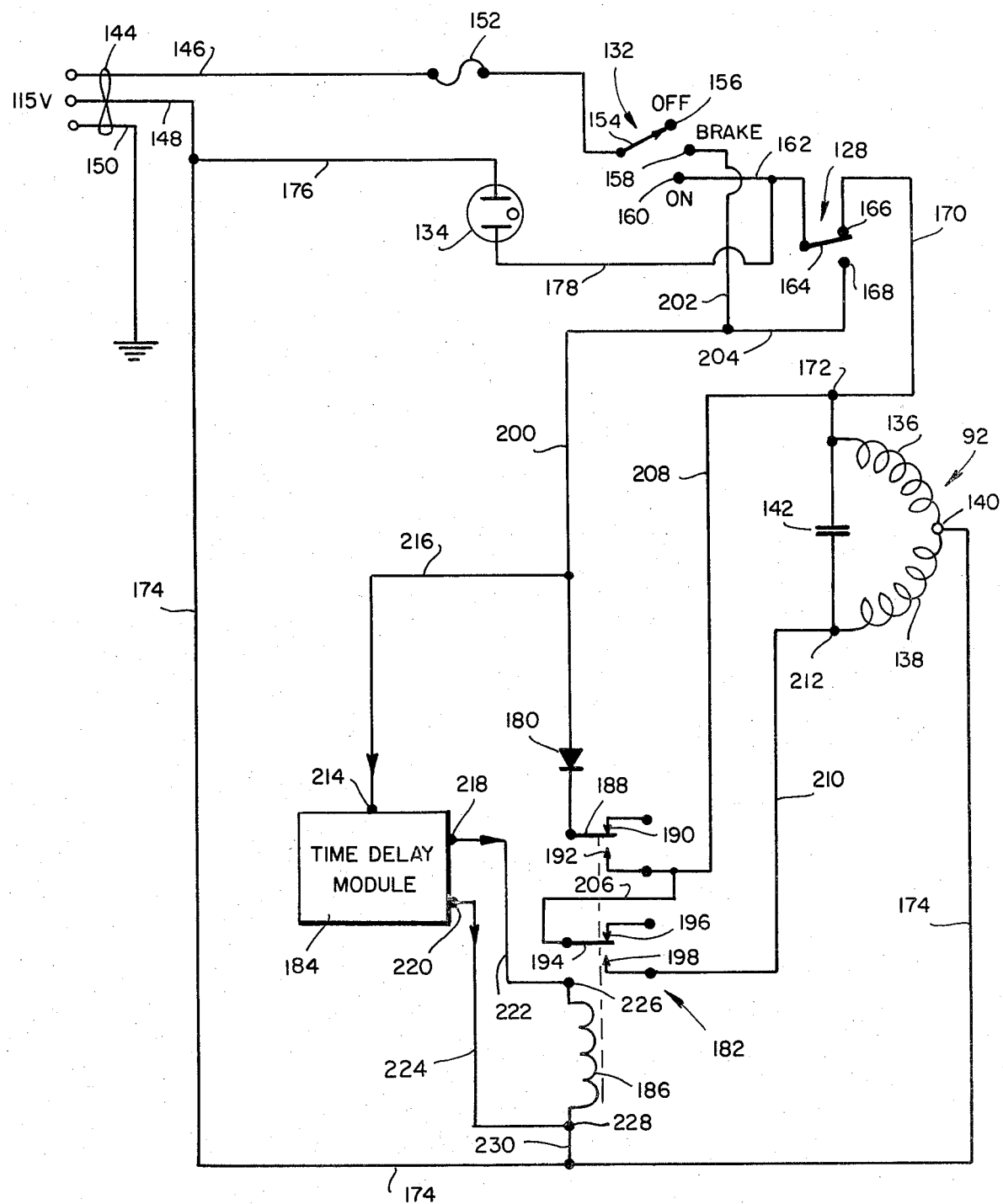
FIG. 6 is a schematic circuit diagram of the electrical circuit employed to energize the drive motor and the dynamic braking means associated therewith.

FIG. 6 illustrates schematically the electrical circuit for the centrifuge 10. The electric motor 92 which drives the centrifuge rotor 112 is of a split-phase type having armature windings 136, 138 connected at one end to a common terminal 140, with the opposite ends thereof connected to opposite ends of a capacitor 142 which is mounted exteriorly of the motor on the bottom wall 38 of base housing 26, as shown in FIG. 2.

The electrical circuit includes an input cable 144 adaptable for connection to a 115 volt, 60 HZ electrical power source. The cable 144 includes input leads 146, 148 and ground lead 150. The lead 146 is connected through a fuse 152 to the contact arm 154 of rotary switch 132, which contact arm 154 is movable selectively to a fixed contact 156 representing the "Off" switch position, a fixed contact 158 representing the "Brake" switch position, and a fixed contact 160 representing the "On" switch position. The "On" contact 160 is connected through lead 162 to the movable contact arm 164 of safety switch 128, the latter having a fixed contact 166 which is engaged by the contact arm 164 when the cover 54 is in closed position, and a fixed contact 168 which is engaged by contact arm 164 when the cover is in open position. The contact 166 is connected through lead 170 to motor input terminal 172 which is connected to the junction of capacitor 142 and armature winding 136. The terminal 140 is connected through return lead 174 to cable input lead 148.

In operation, when the cover 54 is in closed position and rotary selector switch 132 is turned to the "On" position, current flows through lead 146, switch arm 154, switch contact 160, lead 162, switch arm 164, contact 166, and lead 170, to motor input terminal 172. At this point, the current divides into a first current flow through armature winding 136 and a second current flow through capacitor 142 and armature winding 138 which is shifted in phase relative to the current flow through winding 136. The total armature current through windings 136 and 138 then flow from terminal 140 through return lead 174 to input lead 148. In this condition, the motor 92 is driven at high speed.

The indicator lamp 134 is connected by leads 176 and 178 between input lead 148 and lead 162, so that lamp 134 is energized when movable contact arm 154 of switch 132 is in engagement with the "On" contact 160.

The motor braking means includes a diode 180, a relay 182 and an associated time delay module 184 which are mounted within the base housing 26. As previously indicated, the braking means is operable either when the rotary selector switch 132 is turned to the "Brake" position, or when the hinged cover 54 is raised to actuate safety switch 128.

Relay 182 includes an actuating coil 186, a first set of contacts comprising an arm 188 movable between contacts 190 and 192, and a second set of contacts comprising an arm 194 movable between contacts 196 and 198. The arms 188 and 194 are mechanically coupled to move in unison in response to energization of the coil 186. In the deenergized condition of coil 186, the arms 188 and 194 are biased to engage the respective contacts 190 and 196, as shown in FIG. 6.

The anode of diode 180 is connected by leads 200 and 202 to the "Brake" contact 158 of rotary switch 132, and is also connected by leads 200 and 204 to the fixed contact 168 of safety interlock switch 128. The cathode of diode 180 is connected to the movable contact arm 188 of relay 182. Movable contact arm 194 is connected by lead 206 to fixed contact 192 and both are connected by lead 208 to the motor input terminal 172. Contact 198 is connected by lead 210 to the junction 212 of capacitor 142 and armature winding 138.

The input terminal 214 of time delay module 184 is connected by leads 216, 200 and 202 to "Brake" contact 158 of selector switch 132, and by leads 216, 200 and 204 to the fixed terminal 168 of safety interlock switch 128. The output terminals 218 and 220 of time delay module 184 are connected to opposite ends 226 and 228 of relay actuating coil 186 by respective leads 222 and 224. The coil end 228 is connected by lead 230 to return lead 174.

In operation, when the motor 92 is rotating and the rotary selector switch is turned to the "Brake" position, with its contact arm 154 in engagement with fixed contact 158, current flows through lead 146, arm 154, contact 158, leads 202, 200 and 216 to input terminal 214 of time delay module 184, thereby causing module 184 to produce an output current flow through relay actuating coil 186, thereby moving relay contact arms 188 and 194 into engagement with respective contacts 192 and 198. At the same time, current from lead 200 flows through diode 180 as rectified half-wave current which is supplied through relay contact arm 188, fixed contact 192, lead 208, and input terminal 172 to armature winding 136. This rectified half-wave current is also supplied to the other armature winding 138 via contact arm 188, contact 192, lead 206, contact arm 194, fixed contact 198, lead 210, and junction 212. The current through armature windings 136, 138 is summed at the common terminal 140 and is returned to input lead 148 via return lead 174. The foregoing operation of the relay 182 thus results in short circuiting of capacitor 142 and the application of unidirectional current through armature windings 136 and 138 which creates a strong magnetic field which acts upon the rotor of the motor 92 to brake its rotation. This magnetic field thus creates a dynamic braking effect which is effective to stop rotation of the rotor completely within six to ten seconds after application.

In order to prevent prolonged application of unidirectional current to the motor armature windings 136 and 138, which may cause motor overheating, the time delay module 184 is operative to deenergize the relay 182 after a selected time period which is preferably twenty seconds. Thus, when current is applied through leads 204, 200 and 216 to the input terminal 214 of the time delay module 184, the relay coil 186 is energized by the module output terminals 218 and 220 for a timed period of approximately twenty seconds to brake the motor 92, after which the output current of the module 184 is cut off to deenergize the relay coil 186. The relay contact arms 188 and 194 therefore are biased out of engagement with the respective contacts 192 and 198 and into engagement with the respective contacts 190 and 196, thereby interrupting the path of unidirectional current flow from diode 180 to the motor armature windings 136 and 138.

The same dynamic braking effect, as described above, is independently effected when the hinged cover 54 is lifted while the motor is running. When the cover 54 is elevated, with the rotary selector switch 132 in the "On" position, the arm 164 of safety interlock switch 128 is biased out of engagement with contact 166 and into engagement with contact 168. Current from input lead 146 thus flows through contact arm 154, contact 160, lead 162, contact arm 164, contact 168, lead 204 and lead 200 to the time delay module 184 and diode 180, for application of dynamic braking to the motor 92, as previously described.

While a preferred embodiment of the invention has been shown and described herein, it is obvious that numerous omissions, charges and additions may be made in such embodiment without departing from the spirit and scope of the invention.

What is claimed is:

1. A high speed centrifugal concentrator comprising a housing divided into a vacuum chamber and a base section,
   said vacuum chamber having side and bottom walls, a cover constituting the top wall thereof, and means pivotally mounting one end of said cover on said vacuum chamber for movement between an upstanding open position and a closed position in which it closes off said vacuum chamber in sealed, air-tight condition,
   a centrifuge rotor,
   means mounting said centrifuge rotor for rotation within said vacuum chamber, said mounting means including a mounting shaft journalled on said vacuum chamber and secured to said rotor,
   an electric drive motor for said centrifuge rotor mounted within said base section externally of said vacuum chamber and remote therefrom,
   electric circuit means for controlling the operation of said motor and including means for dynamically braking said motor,
   magnetic coupling means for providing a magnetic drive connection between said motor and said centrifuge rotor and creating a magnetic field passing through a wall of said vacuum chamber, whereby said centrifuge rotor is rotated within said vacuum chamber in response to operation of said drive motor,
   said magnetic coupling means comprising a first permanent magnet member secured to said mounting shaft and having a plurality of permanent magnets mounted thereon, and a second permanent magnet member secured to the drive shaft of said motor and having a corresponding member of permanent magnets of opposite polarity mounted thereon,
   and a safety interlock switch mounted on said vacuum chamber and operatively associated with said cover for energizing said means for dynamically braking said drive motor when said cover is in its open position.

2. A high speed centrifugal concentrator according to claim 1 which includes means for creating a vacuum condition within said vacuum chamber while said drive motor is operating to rotate said centrifuge rotor.

3. A high speed centrifugal concentrator according to claim 1 in which said vacuum chamber overlies the top end of said base section and is formed with a well depending into the interior of said base section, with a cover plate overlying the top end of said well, said mounting shaft being journalled in said cover plate and having an upper portion extending above said cover plate and a lower portion depending from said cover plate into the interior of said well, and means for removably mounting said centrifuge rotor on the upper portion of said mounting shaft.

4. A high speed centrifugal concentrator according to claim 3 in which said first and second permanent magnet members are closely spaced from opposite surfaces of the bottom wall of said well and arranged to create a magnetic field through said bottom wall whereby said permanent magnet members are magnetically attracted to each other.

5. A high speed centrifugal concentrator according to claim 4 in which each of said first and second permanent magnet members comprises a disc having a plurality of permanent magnets embedded therein.

6. A high speed centrifugal concentrator according to claim 1 in which said drive motor is a split phase motor having a plurality armature windings and a rotor, and in which said electrical circuit has a first branch for selectively applying alternating current to said armature windings, and a second branch for selectively applying unidirectional current to said armature winding whereby to magnetically brake the rotation of said motor rotor.

7. A high speed centrifugal concentrator according to claim 6 in which said second circuit branch includes rectifier means for converting said alternating current into unidirectional current, and switching means for applying said unidirectional current to said armature windings for creating a magnetic field between said windings and said motor rotor.

8. A high speed centrifugal concentrator according to claim 7 in which said second circuit branch also includes time delay means for controlling operation of said switch means, said time delay means being in circuit with said switch means and being operative to cause said switch means to interrupt the application of unidirectional current to said armature windings after a predetermined time interval.

9. A high speed centrifugal concentrator according to claim 6 in which said electrical circuit means includes a manually-operable selector switch having an "Off" position in which it interrupts all current flow to said motor armature windings, an "On" position in which it energizes said first circuit means to apply alternating current to said armature windings, and a "Brake" position in which it deenergizes said first circuit branch and energizes said second circuit branch to apply unidirectional current to said armature windings.

10. A high speed centrifugal concentrator according to claim 9 in which said safety interlock switch has a first position in which it completes said first circuit branch, to energize said motor when said cover is in closed position and said selector switch is in "On" position, and a second position in which it interrupts said first circuit branch and completes said second circuit branch to brake said motor when said cover is raised from its closed position with said selector switch in "On" position.

* * * * *

REEXAMINATION CERTIFICATE (1368th)
United States Patent [19]
Vilardi

[11] B1 4,226,669
[45] Certificate Issued   Oct. 16, 1990

[54] VACUUM CENTRIFUGE WITH MAGNETIC DRIVE

[75] Inventor: Frank Vilardi, Nesconset, N.Y.

[73] Assignee: Savant Holdings, Inc., Farmingdale, N.Y.

Reexamination Request:
No. 90/001,964, Mar. 19, 1990

Reexamination Certificate for:
Patent No.: 4,226,669
Issued: Oct. 7, 1980
Appl. No.: 37,429
Filed: May 9, 1979

[51] Int. Cl.$^5$ .............................................. B01D 1/00
[52] U.S. Cl. ............................. 159/6.1; 192/84 PM; 200/61.7; 159/44; 494/10; 494/11; 494/12; 494/16; 494/61; 494/84

[56] References Cited

U.S. PATENT DOCUMENTS

| | | |
|---|---|---|
| 2,514,342 | 4/1950 | Schoenbaum. |
| 3,080,303 | 3/1963 | Nerheim. |
| 3,085,407 | 4/1963 | Tomlinson. |
| 3,281,362 | 10/1966 | Ozaki. |
| 3,304,990 | 2/1967 | Ontko et al. |
| 3,504,777 | 4/1970 | Waugh ............................... 200/61.7 |
| 3,975,668 | 8/1976 | Davie. |
| 4,010,893 | 3/1977 | Smith et al. |

OTHER PUBLICATIONS

"Installation, Operation, and Service Manual for General Purpose Refrigerated Centrifuge Model 5000," Cat. No. 2345/2346 (International Equipment Co., Div. of Damon, Needham Heights, Ma., Jun. 1975), pp. 1–3, 3–3, 3–4, 4–6.
"The Beckman Model J-21B Preparative Centrifuge Instruction Manual," J21B-IM-2A (Beckman Instruments Inc., Feb. 1974), pp. 1–3, 1–14, 2—2, 2–3, 2–4, 2–5, 3–2, 3—3, 4–15.
"Standard Handbook For Electrical Engineers", (McGraw-Hill Book Co., Inc., 1949), p. 1711.

*Primary Examiner*—Kenneth M. Schor

[57] ABSTRACT

A high speed centrifugal concentrator includes a vacuum chamber within which a centrifuge rotor is rotatably mounted for spinning a plurality of vials containing biological solutions or the like at high speed while subjecting the solution to a vacuum condition for concentrating and evaporating the latter. The vacuum chamber has a hinged cover and is completely enclosed to maintain the vacuum condition therein and the centrifuge rotor is driven by an electric motor located outside of said closed vacuum chamber and remote therefrom. The electrical circuit for driving the motor includes dynamic braking means for braking the motor in response to manual operation of a selector switch, or to the raising of the vacuum chamber cover from closed position.

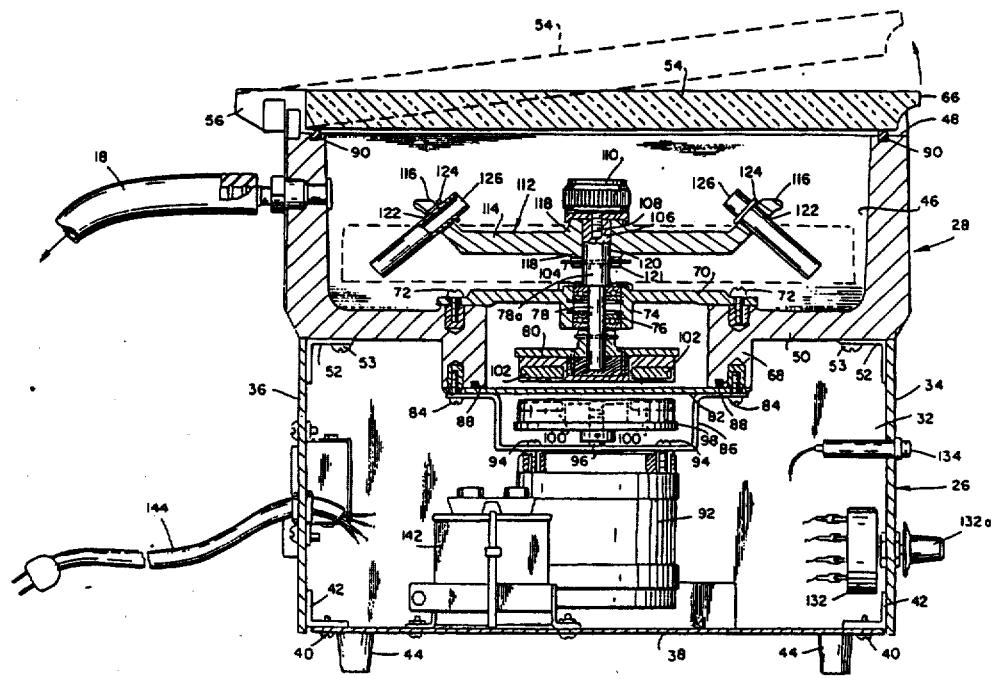

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-10 is confirmed.

* * * * *